United States Patent
Campbell et al.

(10) Patent No.: US 6,669,627 B1
(45) Date of Patent: Dec. 30, 2003

(54) REM SLEEP AUGMENTATION WITH EXTRA-OCULAR LIGHT

(75) Inventors: Scott S. Campbell, Chappaqua, NY (US); Patricia J. Murphy, Chappaqua, NY (US)

(73) Assignee: Cornell Research Foundation Inc., Ithaca, NY (US)

( * ) Notice: Subject to any disclaimer, the term of this patent is extended or adjusted under 35 U.S.C. 154(b) by 0 days.

(21) Appl. No.: 09/937,324

(22) PCT Filed: Jul. 7, 2000

(86) PCT No.: PCT/US00/18820
§ 371 (c)(1),
(2), (4) Date: Sep. 20, 2001

(87) PCT Pub. No.: WO01/03751
PCT Pub. Date: Jan. 18, 2001

Related U.S. Application Data
(60) Provisional application No. 60/143,217, filed on Jul. 9, 1999.

(51) Int. Cl.[7] .............................................. A61M 21/00
(52) U.S. Cl. ....................................................... 600/27
(58) Field of Search ............. 600/26–27; 128/897–899; 607/1, 88, 91

(56) References Cited

U.S. PATENT DOCUMENTS

| | | |
|---|---|---|
| 3,670,193 A | 6/1972 | Thorington et al. |
| 4,600,723 A | 7/1986 | Short et al. |
| 4,858,609 A | 8/1989 | Cole |
| 4,893,291 A | 1/1990 | Bick et al. |
| 5,000,752 A | 3/1991 | Hoskin et al. |
| 5,047,006 A | 9/1991 | Brandston et al. |

(List continued on next page.)

FOREIGN PATENT DOCUMENTS

| | | |
|---|---|---|
| EP | 233962 | 5/1925 |
| EP | 0 469 227 A1 | 2/1990 |
| EP | 0 736 307 A2 | 10/1996 |
| WO | WO 95/19809 | 7/1995 |
| WO | WO 95/25563 | 9/1995 |
| WO | WO98/51372 | 11/1998 |

OTHER PUBLICATIONS

Campbell, et al., "Extraocular Circadian Phototransduction in Humans," Science, 279:376–9, Jan. 16, 1998.

Bloch, et al., "Interaction between Post–Trial Reticular Stimulation and Subsequent Paradoxical Sleep in Memory Consolidation Processes," in Neurobiology of Sleep and Memory, Drucker–Colin and MacGaugh, eds., New York: Academic Press, 1977, pp. 255–272.

Drucker–Colin, et al., "Increasing PGO spike density by auditory stimulation increases the duration and decreases the latency of rapid eye movement (REM) sleep," in Brain Research, 278:308–12, 1983.

(List continued on next page.)

*Primary Examiner*—Max F. Hindenburg
*Assistant Examiner*—Joseph A. Cadugan
(74) *Attorney, Agent, or Firm*—Darby & Darby (57) ABSTRACT

The invention provides for exposing an extraocular (i.e., non-ocular) region of a human to light during sleep which enhances REM sleep. Also provided are devices to carry out the methods. Key timing parameters ensure effective REM enhancement without adversely impacting a subject's circadian clock. The invention provides for improving cognitive function and performance in healthy individuals, and in individuals suffering from a disease or disorder in which mental status is compromised. One embodiment of the invention (100) includes a fiber optics pad (160) attached to a power source, and lamp housing (120) by a fiber optics cable (140).

22 Claims, 6 Drawing Sheets

U.S. PATENT DOCUMENTS

| | | | |
|---|---|---|---|
| 5,079,682 A | | 1/1992 | Roberts |
| 5,086,770 A | | 2/1992 | Prangley |
| 5,140,562 A | | 8/1992 | Moore-Ede et al. |
| 5,149,184 A | | 9/1992 | Hughes et al. |
| 5,163,426 A | | 11/1992 | Czeisler et al. |
| 5,167,133 A | | 12/1992 | Schmidt |
| 5,167,228 A | | 12/1992 | Czeisler et al. |
| 5,169,380 A | | 12/1992 | Brennan |
| 5,176,133 A | | 1/1993 | Czeisler et al. |
| 5,197,941 A | | 3/1993 | Whitaker |
| 5,242,941 A | | 9/1993 | Lewy et al. |
| 5,259,830 A | | 11/1993 | Masuda |
| 5,265,598 A | * | 11/1993 | Searfoss et al. ............... 607/88 |
| 5,292,345 A | | 3/1994 | Gerardo |
| 5,300,097 A | | 4/1994 | Lerner et al. |
| 5,304,212 A | | 4/1994 | Czeisler et al. |
| 5,327,331 A | | 7/1994 | Roberts |
| 5,343,121 A | | 8/1994 | Terman et al. |
| 5,358,503 A | | 10/1994 | Bertwell et al. |
| 5,441,528 A | | 8/1995 | Chang et al. |
| 5,447,528 A | | 9/1995 | Gerardo |
| 5,489,279 A | | 2/1996 | Meserol |
| 5,503,637 A | | 4/1996 | Kyricos et al. |
| 5,507,716 A | * | 4/1996 | LaBerge et al. ............... 600/27 |
| 5,545,192 A | | 8/1996 | Czeisler et al. |
| 5,551,879 A | * | 9/1996 | Raynie et al. ............... 434/236 |
| 5,562,719 A | | 10/1996 | Lopez-Claros |
| 5,589,741 A | | 12/1996 | Terman et al. |
| 5,616,140 A | | 4/1997 | Prescott |
| 5,648,656 A | | 7/1997 | Begemann et al. |
| 5,716,978 A | | 2/1998 | Lewy et al. |
| 5,766,233 A | | 6/1998 | Thiberg |
| 5,824,024 A | | 10/1998 | Dial |
| 5,899,206 A | | 5/1999 | La Chappelle-Reynolds |
| 6,135,117 A | | 10/2000 | Campbell et al. |
| 6,164,787 A | * | 12/2000 | Seki et al. ...................... 362/1 |
| 6,350,275 B1 | * | 2/2002 | Vreman et al. ............... 607/88 |

OTHER PUBLICATIONS

Guerrien, et al., "Enhancement of Memory by Auditory Stimulation During Postlearning REM Sleep in Humans," in Physiology & Behavior, 45: 947–50, 1989.

O. Mandai, "REM Sleep Modifications after a Morse Language Learning Session," in Sleep '86, Koella, Obal, Schulz & Visser eds., New York: Gustav Fischer Verlag, 1988, pp. 382–384.

H. Merchant–Nancy, et al., "Brain Distribution of c–fos expression as a result of prolonged rapid eye movement (REM) sleep period duration," in Brain Research, 681: 15–22, 1995.

J. Vazquez, et al., "The Effects of Sensory Stimulation on REM Sleep Duration," in Sleep, 21:138–42, 1998.

A. Borbely & H.U. Neuhaus, "Circadian Rhythm of Sleep and Motor Activity in the Rat During Skeleton Photoperiod, Continuous Darkness and Continuous Light," in J. of Comparative Physiology, 128:37–46, 1978.

L. De Gennaro, et al., "Increase of REM Duration and Decrease of REM Latency after a Prolonged Test of Visual Attention," in J. Neuroscience, 82: 163–68, 1995.

M.F. Bennett, *Handbook of Sensory Physiology*, "Extra Ocular Light Receptors and Ciroadian, Rhythms", vol. 7–6a:641–663 (1979).

B. Iyengar, Experientia, "Indoleamlnes and the UV–light–sensitive photoperiodic responses of the melanocyte network; a biological calendar?" vol. 50, No. 8, pp. 733–736 (1994).

J.J. Wolken et al., Photochemistry and Photobiology, "Extra–Ocular Photosensitivity", Pergamon Press Ltd., Great Britain, vol. 29, pp. 189–196 (1979).

The Neuroscientist, vol. 2, 1996, Dan A. Oren, "Humoral Phototransuction: Blood Is a Messenger".

Laboratory of Human Chronobiology, Department of Psychiatry, Cornell University Medical College Scott Campbell and Patricia Murphy, "Extraocular Circadian Phototransuction in Humans" submitted Science Aug. 11, 1997.

Cellt & Tissue Research, vol. 285, No. 3, Sep. 1996, Stefan Reuss, "Compounds and Connections of the Circadian Timing System in Mannals".

Expansion Scientifique Francaise, Pathologie Biologie, vol. 44, No. 6, Jun. 1996, Synchronisation ET Dyschronisme Des Rythmes Circadiens Humains.

Brazilian Journal of Medical and Biological Research, vol. 29(1) 1–1148, Jan. 1996, D.A. Golombek and M.R. Ralph, "Let There Be Light: Signal Transduction In a Mammalian Circadian System".

The New England Journal of Medicine, vol. 332, Jan. 5, 1995, No. 1, Czeisler, Charles A., "Suppression of Melatonin Secretion In Some Blind Patients By Exposure To Bright Light".

Current Directions In Psychological Science, vol. 2, No. 2, pp. 34–39, Apr. 1993, Russel G. Foster, "Photoreceptors and Circadian Systems".

Acta Anatomica, Aug. 1992; 144:332–335, B. Iyengar, "Melanocytes–A UV–Sensitive Neural Network and Circadian Rhythms".

Nature International Weekly Journal of Science, vol. 350, No. 6313, Mar. 1991, A.T. Winfree, p. 18, "Resetting The Human Clock".

The New Journal of Medicine, vol. 322, May 1990 No. 18, P 1306–1308, owned and Published by Massachusetts Medical Society, "Strategies For Resetting The Human Circadian Clock".

Science, vol. 244, Jun. 1989, pp. 1328–1333, Charles A. Cziesler et al. "Bright Ligfht Inductions of Strong (Type 0) Resetting of the Human Circadian Pacemaker".

Am/Psychiatry 144:6, Jun. 1987 pp. 753–757, Thomas A. Wehr, "Eye Versus Skin Phototherapy of Seasonal Affective Disorder".

Science, vol. 233, Aug. 1986, pp. 667–678, "Bright Light Resets the Human Circadian Pacemaker Independent of the Timing of the Sleep–Wake Cycle".

Perceptual and Motor Skills, Oct. 1985, 61, 343–354, Richard Woodhouse, "Responses of Albino and Hooded Rats to Various Illumination Choices in a Six–Chambered Alleyway".

Dermatologica, 166 : 186–191, 1983, Altmeyer, et al. "Beeinflussung Endokrinlogischer Parameter Durch UV–Ganzbestrahlungen".

The Anatomical Record, Jan. 1973, Scheving et al. "The Persistence of a Circadian Rhythm in Histamine Response in Gjuinea Pigs Maintained Under Continuous Illumination".

Physiology and Behaviour an International Journal vol. 38, No. 4, 1986, pp. 571–574, Thomas J. Savides et al. "Natural Light Exposure of Young Adults".

* cited by examiner

REM SLEEP AUGMENTATION WITH EXTRA-OCULAR LIGHT

This patent application is a 371 of International Application No. PCT/US00/18820 filed Jul. 7, 2000 (published in English), which application claims the benefit of Provisional Application Serial No. 60/143,217 filed Jul. 9, 1999.

The research leading to the present invention was supported in part by the National Institutes of Health Grants R01-AG15370, R01-MH45067, R01-AG12112, R01-MH45617, P20-MH45762, R03-AG15370, K02-MH01099, and M01-RR00047. The United States Government has certain rights in the invention.

FIELD OF THE INVENTION

The invention relates to a non-drug alternative to enhance cognitive function. In particular, the invention provides for exposing an extraocular (i.e., non-ocular) region of a human to light during sleep, which enhances REM sleep. Also provided are devices to carry out the methods. Key timing parameters ensure effective REM enhancement without adversely impacting a subject's circadian clock. The invention provides for improving cognitive function and performance in healthy individuals and in individuals suffering from a disease or disorder in which mental status is compromised.

BACKGROUND OF THE INVENTION

Rapid eye movement, or REM sleep, is a discrete sleep state characterized by muscle atonia (i.e., flaccid paralysis), low voltage, desynchronized EEG, and phasic activity such as increased respiratory activity, muscle twitches and burst of rapid eye movement. In humans, REM sleep comprises about 20–25% of a normal night's sleep and it is during this time that dreams typically occur.

There is a vast body of literature documenting an intimate relationship between the occurrence of REM sleep on one hand, and learning and memory on the other. For example, rodents undergoing intensive water maze learning trials, and humans exposed to high-intensity learning and memory regimens exhibit increased REM sleep amounts in subsequent sleep episodes. Likewise, deprivation of REM sleep inhibits learning and memory on subsequent tasks and retention of learned information is compromised when followed by REM deprivation.

Presentation of auditory, visual, and somatosensory stimuli just prior to or during sleep has been reported to enhance REM sleep in laboratory animals and humans, typically without altering non-REM (NREM) sleep (Block et al., In: Neurobiology of Sleep and Memory, Drucker-Colin and MacGaugh, eds., New York: Academic Press, 1977, pp. 255–72; Drucker-Colin et al., Brain Res. 278:308, 1983; Guerrien et al., Physiol. Beh. 45:947, 1988; Mandai et al., Sleep '86 Sutttgart: Gustav Fischer Verlag, 1988, pp. 3824; Merchant-Nancy et al., Brain Res. 681:15, 1988; Vazquez et al., Sleep 21:138, 1988). One sensory stimulus that has not been tested in this regard is photic stimulation. Although rats maintained in conditions of constant light exhibit more REM sleep per 24 hours (Vazquez and Neuhaus, J. Comp. Physiol. 128:37, 1978), there is no report of alteration of REM sleep by administration of a pulse of light during sleep. Naturally the disruptive effect on sleep of light administration to the eyes argues against conducting such a study at all.

In previous work, the inventors have shown that light applied to the popliteal fossa (the area directly behind the kneecap) can affect the biological clock in the same way as light presented to the eyes (co-owned, co-pending U.S. patent application No. 09/074,455 and International Application No. PCT/US98/09550, Publication No. WO 98/51372, filed May 7 and 11, 1998, respectively, both entitled "Non-ocular Circadian Clock Resetting in Humans"; Campbell et al., Science 279:376, 1998). However, there was no indication that non-ocular light exposure would in any way affect sleep stages or patterns, and particularly no indication that it could enhance REM sleep.

Moreover, the discovery that non-ocular light exposure can shift the circadian cycle cautions against doing anything that would unintentionally disrupt the circadian cycle in the absence of an external disruption, such as trans-meridian travel or shift work.

As described below, the present invention advantageously permits enhancement of REM sleep, and concomitant enhancement of cognitive function. Moreover, by applying the strategies and devices of the invention, these enhancements can be achieved without adversely modifying the circadian rhythm.

SUMMARY OF THE INVENTION

The present invention advantageously provides a method for enhancing REM sleep in a subject, preferably a human subject. The method comprises exposing a non-ocular region of a subject to photic stimulation for an interval during a sleep period. In particular, this method can increase the number of minutes spent in REM sleep during the interval of photic stimulation, e.g., by increasing the frequency of REM periods. The method of the invention advantageously provides for enhancing cognitive function in a subject, particularly memory processes. Subjects whom the invention can assist include those who suffer from a medical disorder in which mental status is compromised, as well as normal individuals.

In a specific embodiment, the invention provides a method for increasing REM sleep of a person, which method comprises the steps of sensing the start of the REM cycle; sensing the end of the REM cycle; determining the time and interval of the REM cycle; and, augmenting the time interval of the REM cycle by selectively providing non-ocular photic stimulation for a predetermined interval. Also provided is a device or an article for increasing REM sleep of a person. Such an article, which may be adapted to be worn or attached to the person, includes a sensor which provides phasic activity signals; a timing circuit connected to the sensor and outputting an elapsed-interval signal indicative of the magnitude of the REM cycle; a comparator which compares the elapsed-interval signal to a predetermined-interval signal and outputs a shortfall signal; a controller responsive to the shortfall signal to generate a control signal; and, a photic stimulator positionable in contact with the person's skin and being actuated in response to the control signal.

DESCRIPTION OF THE DRAWINGS

FIGS. 2A, B, and C. Views of a light-emitting diode (LED) array device for exposing skin to light. 2A. View of the complete device. 2B. View of diode array. 2C. Perspective view of the device attached to the popliteal fossa.

DETAILED DESCRIPTION

The present invention is based, in part, on the recent discovery that non-ocular (i.e., extraocular) presentation of light during sleep can increase REM sleep during the time of exposure by at least about 30%, and by as much as about 200%, with an average of about 50%. Enhancement of REM sleep results from an increase in the frequency of REM periods, e.g., by about 40%. This REM sleep enhancement was found to occur over the entire period of light administration, up to the entire sleep period. No other sleep stages were significantly affected during light administration, nor was sleep architecture altered following the light interval.

These results confirm that extraocular light is transduced into a signal that is received and processed by the human central nervous system. This unexpected and robust finding has potentially important implications in a number of areas. Perhaps the most exciting involves the treatment of cognitive deficits associated with Alzheimer's Disease (AD) and other dementing illnesses, as well as major depression. The current treatment strategy for improving mental functioning in such disorders involves the use of a class of medications referred to as cholinergic agonists, which have their effect by increasing the bioavailability of acetylcholine in the brain. Unfortunately, these drugs have unwanted side effects, particularly in older individuals.

Because it is well demonstrated that REM sleep is mediated by cholinergic activity in the brainstem, our working hypothesis is that extra-ocular light activates cholinergic pathways in the pons, as well as other areas of the brain including the suprachiasmatic nuclei (i.e., the biological clock). Thus, although not intending to be limited by any particular theory, we hypothesize that extra-ocular light presented during sleep will have the same effect on the cholinergic system as the currently used medications. However, the effects mediated by extra-ocular light can be achieved, without the side effects associated with such medications and complications of interactions with other medications. In addition, compliance problems with the treatment regimen will be reduced or eliminated, since light is administered during sleep. The result is enhanced REM sleep and, consequently, enhanced waking function.

Cognitive performance can be enhanced in healthy individuals of all ages by increasing the amount of REM sleep in a nighttime sleep period. Medications that affect the cholinergic system are not appropriate for healthy individuals. Thus, any individual who requires, or desires, enhanced waking function stands to benefit from this discovery.

A non-drug alternative to enhance cognitive functioning has significant appeal, both with respect to treatment of medical disorders in which mental status is compromised, and in terms of general use for boosting productivity.

The invention thus has broad applicability for mentally impaired and normal individuals. This invention is particularly useful in the timing of photic stimulation, relative to the disclosures of co-owned, co-pending U.S. patent application Ser. No. 09/074,455 and International Application No. PCT/US98/09550 (PCT Publication No. WO 98/51372), filed May 7 and 11, 1998, respectively, both entitled "Non-ocular Circadian Clock Resetting in Humans", the disclosures of each of which are incorporated herein by reference in their entirety. Preferably, to enhance REM sleep and cognitive function with minimum impact on the circadian clock, exposing a non-ocular region to photic stimulation occurs both before and after the critical inflection point during sleep: daily minimum body temperature. This point is achieved at roughly the same time for each individual, although the time can vary widely between individuals. The advantage of providing photic stimulation before and after this point is that biological clock resetting is minimized, since the prior and subsequent exposures offset each other's effects. The devices of the invention advantageously control for the timing of exposure to avoid circadian clock resetting.

Definitions

"REM sleep" refers to the period of sleep characterized by specific phasic activities, including rapid eye movement (REM), flaccid paralysis (decreased muscle tone), middle ear muscle activity, twitching of the extremities (such as the big toe), etc. This is the sleep cycle in which most dreams occur. REM sleep generally occurs in regular intervals of about 90 minutes, and lasts about 20 minutes. Increasing the amount of REM sleep has positive effects on cognitive function, particularly on memory processes. The present invention increases the frequency of REM episodes, i.e., it decreases the interval to less than 90 minutes. By shortening this cycle time, the invention increases the total number of REM episodes, and thus the total amount of REM sleep. It may also be possible to increase the length of a REM episode or episodes. The increase in REM sleep appears to be offset for the most part by a decrease in stage 2 sleep, and to some degree stage 1 sleep.

"Cognitive function" includes, but is not necessarily limited to, the ability to reason and solve problems, short term and long term memory processes, visual discrimination and perceptual skill, and learning.

A "medical disease or disorder in which mental status is compromised" can include a neurodegenerative disease, such as Alzheimer's Disease, Parkinson's Disease, and senile dementia; major depression; schizophrenia; stroke;

childhood learning disorders such as attention deficit disorder (ADD) and, possibly, dyslexia (in which improvement may result from increasing compensation skills rather than directly correcting dyslexia); alcohol and drug abuse; and normal aging.

A "normal" individual is a person whose cognitive function and overall mental status is within normal ranges, and who would not be diagnosed with or assessed as having a disease or disorder in which mental status is compromised.

A "subject" is any animal, preferably a mammal, and more preferably a human, who undergoes or experiences REM sleep. The term "subject" specifically excludes newborns suffering from hyperbilirubinemia, who receive 24-hour light therapy for a few days to two weeks after developing jaundice. In addition to humans, which are exemplified herein, the methods of the invention are expected to enhance REM sleep and cognitive function in any animal that undergoes REM sleep, such as but not limited to, dogs, cats, horses, circus animals, etc., particularly to enhance learning during training of the animal. Thus, although the focus of the methods and devices of the invention is on modulation of REM sleep in humans, it can be extended to other animal species, particularly the species enumerated above.

The terms "non-ocular" and "extra-ocular" refer to any part of the body besides the eyes. It is possible that during the sleep period a subject may observe the light source. However, such visual stimulation would not alter the invention, since by definition the person stimulated visually must be conscious, not asleep. The REM enhancement occurs in sleeping individuals. Preferably, the non-ocular region has ample surface vasculature, so that light-responsive factors present in blood can react to the photic stimulation. Non-ocular regions of the body include, but are by no means limited to, the ear/inner ear; feet, especially the top surface of the feet; arms, especially the inner elbow; legs, especially the inner knee (popliteal fossa); and abdomen. The head is also rich in vasculature, which suggest that cranial exposure may be useful, particularly for people who have lost their hair or have very short or thinning hair. Alternative sites on the head include the forehead, the temples, and the neck. Naturally, the adopted strategy for delivering photic stimulation preferably avoids awaking the subject, so should be administered away from the eyes or in such a way that the eyes are not likely to detect the stimulation.

The term "photic stimulation" as used herein refers to the exposure of a non-ocular region of the body to light, i.e., irradiation by photons. In a specific embodiment, the term "photic stimulation" means non-solar light, i.e., excludes sunlight. For example, solar photic stimulation might occur during a nap on the beach (if such a nap lasted long enough for REM sleep to occur). However, sunlight carried on optical fibers, e.g., from an aperture in an otherwise darkened room, is regarded as non-solar light. Preferably the light is not accompanied by heat. If there is any heat generated by the photic stimulation, it should be minimized. A number of strategies can be used to deliver the photic stimulation, i.e., the light, including fiber optics, light emitting diodes (LEDs), chemiluminescent molecules, etc. Light sources for fiber optics include incandescent, fluorescent, and halogen lamps. Preferably, the photic stimulation is in the visible range, e.g., broad-band white light, more preferably in the blue-green portion of the spectrum (e.g., from about 455 to about 540 nm). It may also be possible to use harmonics of these wavelengths. The intensity of photic stimulation, which depends on the power of the light source and the proximity of the non-ocular region to the light source, can range from about 15 lux to about 150,000 lux, and preferably ranges from about 10,000 lux to about 13,000 lux.

The term "interval" is used herein to refer to the time of photic stimulation. There may be one interval or more than one interval during any sleep period. The interval or intervals have a period of photic stimulation, i.e., light exposure. The duration of an interval of photic stimulation can range from about 15 minutes to about 12 hours; multiple short duration intervals are possible. In a specific embodiment, infra, the duration is about three hours. Preferably, for maximum enhancement of REM sleep, the interval starts when the subject retires to sleep, and continues until the subject arises. This strategy ensures that exposure will proceed and follow the critical inflection point. Alternatively, the interval and duration can be determined by detecting the onset and duration of natural REM sleep, as described below.

The term "sleep period" is used herein to refer to the time in which a subject is asleep, i.e., from the time of falling asleep after going to bed until arising. While sleep periods generally occur at night, REM sleep can be enhanced during daytime sleep as well, e.g., for a shift worker or someone taking a nap. Indeed, shorter sleep periods may be more effective if REM sleep is enhanced.

As used herein, the term "about" or "approximately" means that a value can fall with an acceptable range or acceptable standard deviation for the nature of the particular value and its measurement, e.g., 20%, preferably 10%, more preferably 5%, of a defined value.

Devices for Enhancing REM Sleep

The method described herein requires that a sleeping human subject be exposed to a non-ocular light source under conditions sufficient to enhance REM sleep. Thus, the invention contemplates various devices, apparatus, articles, and the like to supply extraocular light in a controlled manner, i.e., to avoid disrupting circadian rhythms. The terms device, apparatus, and article are used herein interchangeably, although an article can specifically refer to clothing or some other body covering specifically modified to provide non-ocular light.

The invention envisions several different mechanisms for transmission of the light, including but not limited to, fiber optic configurations (see U.S. Pat. No. 5,300,097), light emitting diode (LED) arrays (see U.S. Pat. No. 5,259,380; preferably held on a flexible pad or appliance, e.g., as described in U.S. Pat. No. 5,358,503), and bioluminescent or chemiluminescent derivations. Light sources, e.g., for use with fiber optics, include but are by no means limited to incandescent, halogen, and fluorescent light lamps that produce light in the visible, and preferably blue-green, wavelengths (see U.S. Pat. No. 3,670,193). Preferably, such light sources are part of a device, which may operate on an automatic timer or under computer control.

More preferably, the device includes a feedback mechanism so that exposure occurs during a sleep period for a desired interval. The feedback mechanism may comprise a sensor for detecting phasic activity associated with REM sleep. Through microprocessor control, the frequency and duration of REM sleep can be monitored and, by activating the light source, frequency or duration, or both, of REM sleep modified to increase total REM sleep a desired amount, e.g. by turning on the light to increase the frequency of REM sleep periods. Thus, a device of the invention may be operated by a pre-programmed or programmable microprocessor that regulates the time and interval of light exposure. Such a program can monitor: (1) the length of REM cycles; (2) the length of REM periods; (3) the total amount of REM sleep over a defined time, and judge whether and how much to enhance REM sleep.

In a specific embodiment, controlling exposure of the photic stimulation in response to phasic stimuli can extend the REM period or increase REM frequency, or both. As demonstrated in the examples, non-ocular photic stimulation increases REM frequency (by decreasing the NREM periods).

The sensor for detecting a phasic event can be vibration sensitive, e.g., for toe twitches, or an electromyographic (EMG) electrode to evaluate muscle tone, middle ear muscle activity, eye twitching, or other phasic activity.

A preferred timer element of a device of the invention will function to provide non-ocular photic stimulation for a period that extends through the daily minimum body temperature. This point is achieved at roughly the same time each day for each individual, although the time can vary widely between individuals. In any event, the point of daily minimum body temperature can be calibrated for any given individual and used to set a timer control on the device.

The invention envisions the use of these various devices designed to facilitate light exposure to a wide range of non-ocular sites. For example, a device is envisioned by which the foot or hand is covered (like a sock or glove), thereby exposing the entire area to illumination; another device is one by which the tympanic membrane is illuminated by LEDs incorporated in headphones or earplugs; another device is one by which the midriff is exposed to light by an illuminated wrap; another device is envisioned in which the source of illumination is not worn by the subject but illuminates a non-ocular site, for example, partially-illuminated bed linens.

Energy to operate the aforementioned devices may be provided by a variety of power sources that would enable the devices to be stationary or portable, for example a standard AC outlet or a battery. For example, a 6×4 blue LED array device of the invention can be powered by a battery pack comprising 6 "AA" 1.5 volt batteries, or one or more 9 volt batteries in parallel.

Examples of Devices and Articles to Enhance REM Sleep

Figure 1:
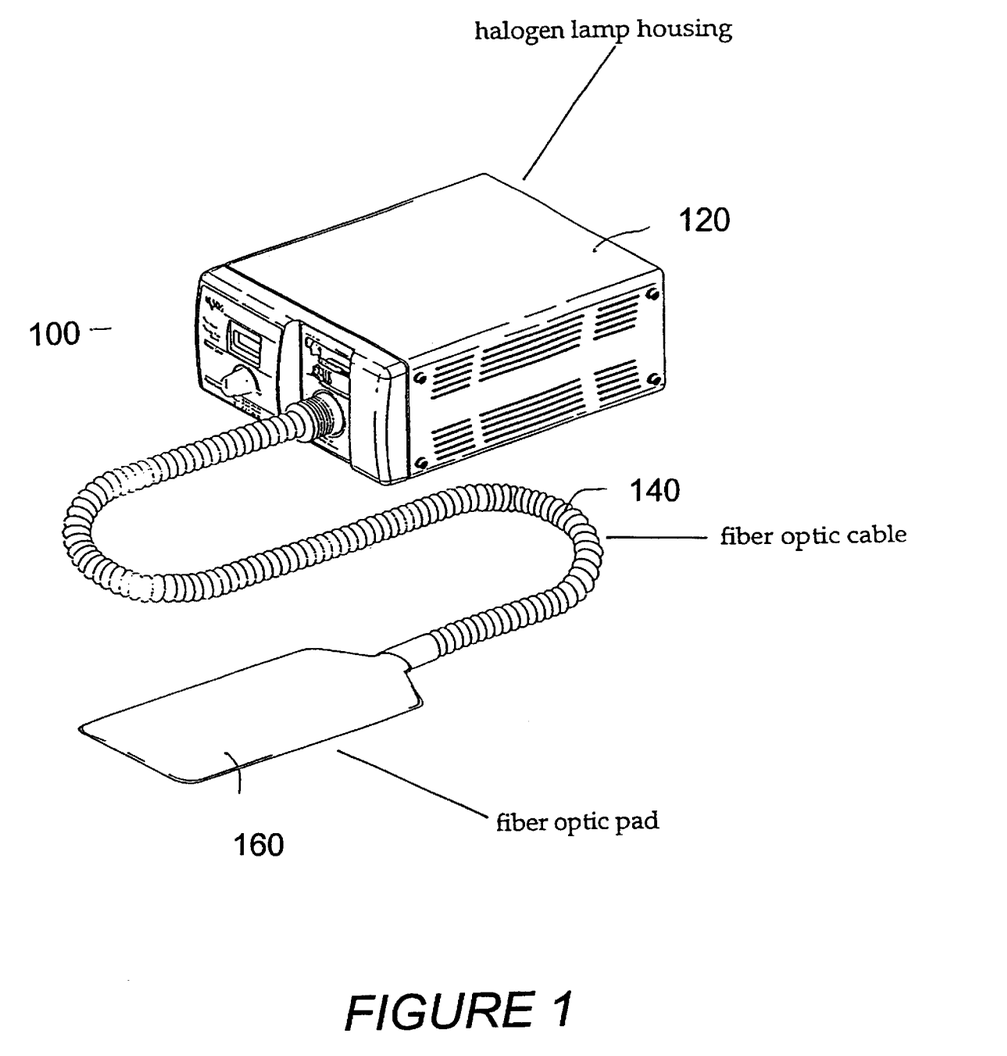
FIG. 1. (Prior art) Perspective view of a device used to expose a non-ocular region of a human subject to light.

The device 100 shown in FIG. 1, which was originally used to reduce the method to practice as described in the example infra, can be altered in a number of ways to facilitate various applications of the method. As described in the Example, the fiber optic pad 160 can be wrapped against the popliteal fossa, or alternatively the inside of the elbow, the calf or thigh, or around the abdomen. Alternatively, this device can be attached to fabric article, such as but by no means limited to, a sheet, blanket, and/or pillow case; undergarments and/or t-shirts; or a nightgown or pajamas (preferably removably attached so that the fabric article can be laundered). Preferably, the fiber optic cable 140 is positioned to minimize contact with the subject. The lamp housing 120 can be plugged into an electrical outlet.

Figures 2A, 2B:
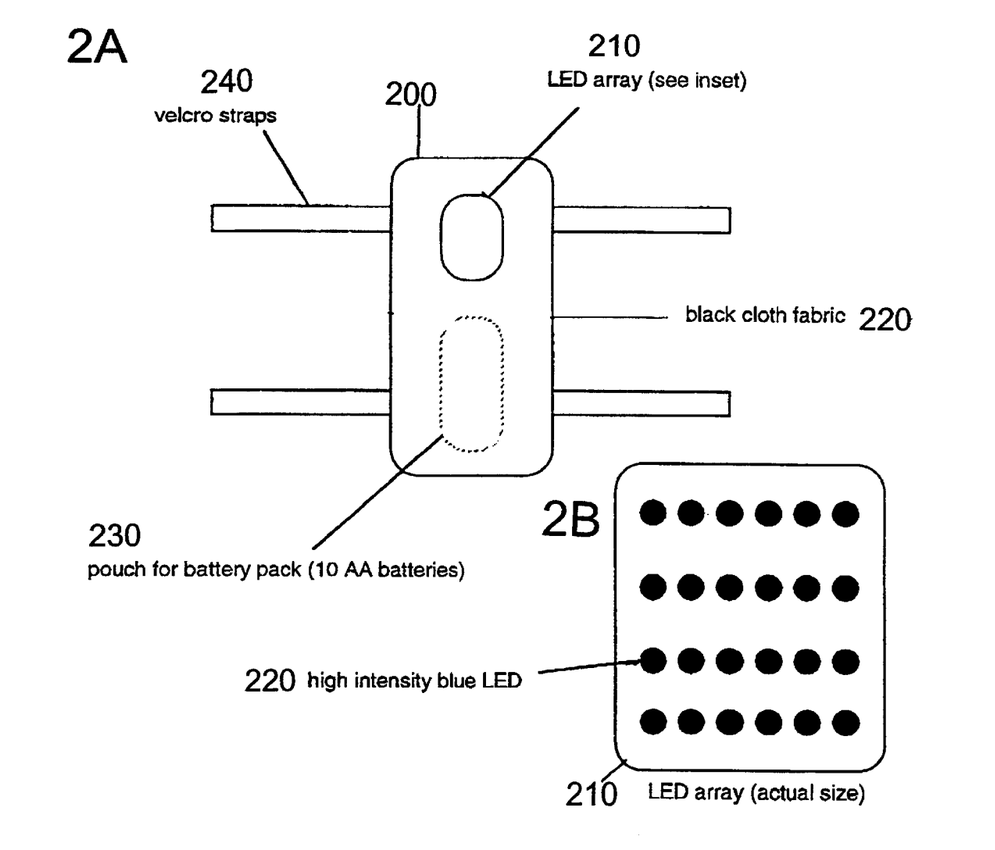
Figure 2C:
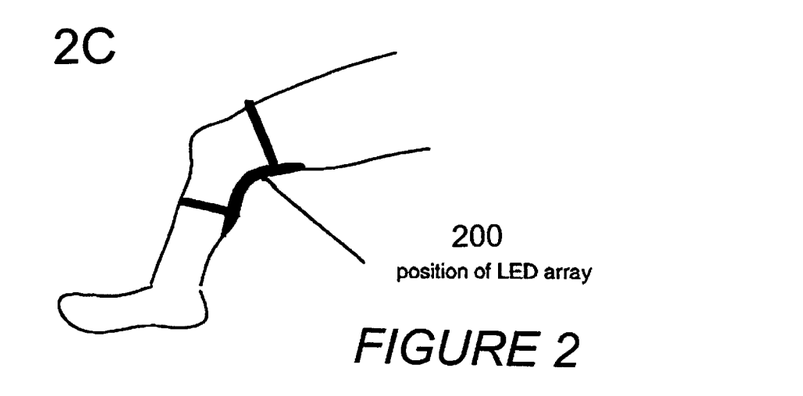

An LED device 200 is shown in FIG. 2A. This device comprises an array 210 of 24 blue, high intensity LEDs 220 (FIG. 2B). The LED array may be supported on a flexible backing 220. In a specific embodiment, the flexible backing can be a black cloth fabric to which the array is adhered with bath tub caulk or an equivalent composition. The array 210 has an area of approximately 2.5"×2.5". It can be run by ten "AA" batteries, or two 9V batteries, placed in pack 230. As shown in FIG. 2C, the LED array and batteries can be strapped onto the leg or other non-ocular region using for example, but not by way of limitation, velcro straps 240, or an elastic wrapping or brace, or sock, e.g., as described below.

Figure 3:
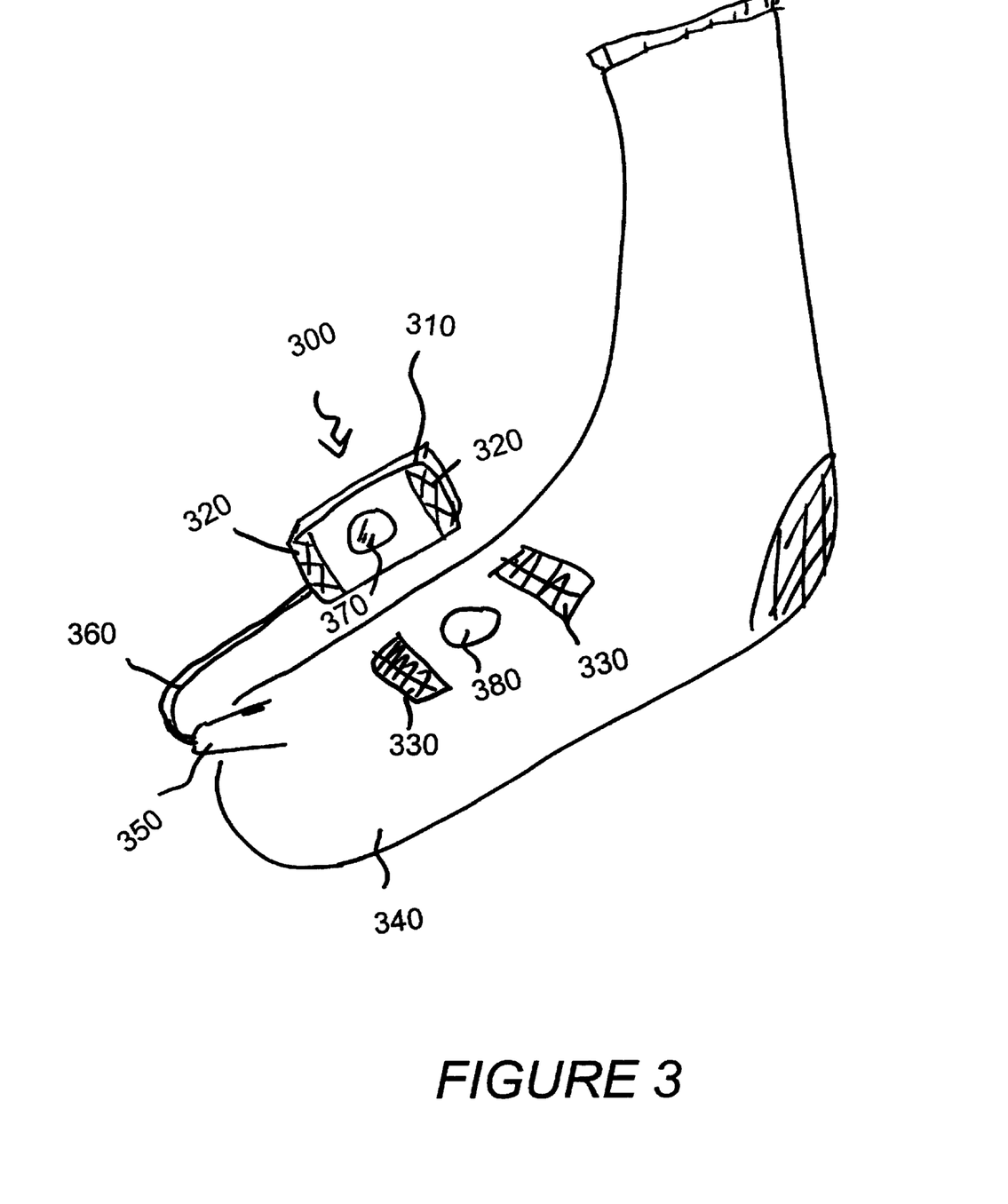
FIG. 3. Perspective view of a sock article for controlled delivery of non-ocular light to the top surface of the foot.

An apparatus in accordance with another aspect of the invention can be worn as an article of clothing, such as a sock, a pair of pajamas, or a band of some sort, or otherwise can be positioned in proximity to a person's skin, for example, through a pillow, sweat band, or chair. With reference to FIG. 3, an article 300 constructed in accordance with this aspect of the invention includes a housing 310 which can be affixed to a person in any conventional manner such as by a strap or by a hook-and-loop attachment to a conventional article of clothing; the manner of attaching the article 300, however, forms no part of the present invention. As shown in FIG. 3, hooks 320 are supported on a front face of the housing and loops 330 are provided on a sock 340. (By placing the loops on the sock, the sock will not stick to other articles of clothing when washed.) The article 300 includes a sensor 350 which is provided to sense the onset and completion of a natural REM cycle. As understood by those of skill in the art, during a REM cycle there are a variety of muscle groups that are active and which can be monitored to gauge the beginning and end of a REM cycle. For example, muscles undergo flaccid paralysis during a REM cycle. Other muscle groups demonstrate twitching phenomenon. Changes from active to inactive and from inactive to active can be monitored to gauge the length of a REM cycle. A presently preferred method monitors the inactive to active transition as indicating the start of a REM cycle and active to inactive as indicating the end of the cycle. For example, a person's toes twitch during REM but not otherwise. The sensor may take on a variety of forms but preferably is suitable for sensing phasic activity, and most preferably is an electromyographic (EMG) electrode.

The sensor 350 communicates with circuitry, for example, circuitry within the housing, by way of an insulated connecting wire 360. The housing further includes a light source which may be within the housing behind a light-transmissive window 370 (as shown) or which may be flush with or project from the housing. In use, the housing 310 is mounted on an article of clothing such as the sock 340 by connecting the hooks 320 to the loops 330 which preferably causes the window 370 or light source to shine directly on the person's skin. Thus, for example, the article of clothing 340 may have an aperture 380 in register with the window 370 or light source, or may have a light-transmissive material positioned to permit light to shine on the person's skin (e.g., the clothing may include stretched rayon or the like).

Figure 4:
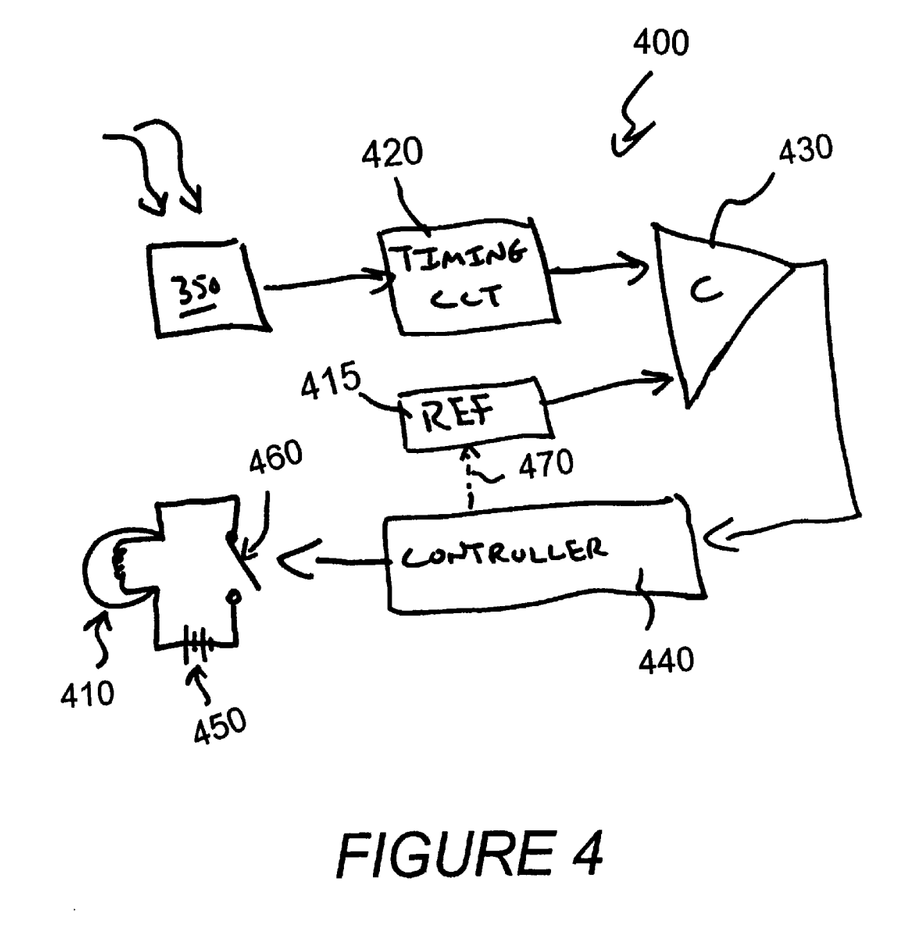
FIG. 4. Block diagram of a circuit for controlling exposer to non-ocular light.

With reference now to FIG. 4, a block diagram of a circuit 400 in accordance with this aspect of the invention is illustrated. The circuit includes the sensor 350 described above and a light source 410 which may be positioned behind the window 370 of the housing 310 or be exposed exteriorly of the housing. The phasic activity detected or sensed by the sensor 350 are provided to a timing circuit 420 for the purpose of determining the length of the person's REM cycle or period of the REM episode, or both. The timing circuit 420 may take on a variety of forms, the particulars of which are not material to the invention. The timing circuit most preferably is implemented using digital circuitry and may comprise a clocking circuit, an interval timer, or pulses stored in a digital circuit from which the passage of time can be gauged by a digital processor.

Alternatively, however, the timing circuit can be implemented using analog components such as an RC timing circuit and voltage detector arrangement as understood by those of skill in the art. In either case, the timing circuit outputs an elapsed-interval signal which is indicative of the magnitude (that is, length) of the REM cycle or REM period, or both.

The elapsed-interval signal is provided as an input to a comparator circuit. The comparator also receives a reference signal from a data store 435, preferably, a reference signal which represents a predetermined-interval of time or other determined interval, as described below. The comparator compares these signals and outputs a shortfall signal which is indicative of the degree to which the person's REM cycle varies in time from the reference signal setting.

A controller 440 responds to the shortfall signal by generating a control signal which, in turn, controls actuation of the light source 410 by completing a circuit which includes the light source 410 and its power supply 450. The circuit is completed by closing a switch 460 which may be a relay switch or transistor. When the light source is positioned in contact with or proximate to the person's skin (e.g., when connected to an article of clothing such as sock 340), the actuated light has an effect on the brain mechanisms controlling sleep of the person such that the REM episode, as detected by the sensor 350, is extended for a period of time thereafter or a new REM episode is initiated sooner.

Optionally, the controller 440 can provide updated information to the data store 350 as the person advances through one or more complete sleep cycles by way of connection 470 (shown in phantom). The updated information can be used to modify the natural period, frequency, or both, of REM sleep.

EXAMPLES

The invention will be better understood by reference to the following examples, which are provided as exemplary of the invention and not by way of limitation.

Example 1

Enhancement of REM Sleep During Extra-ocular Light Exposure

Administration of sensory stimuli just prior to or during sleep has been shown to enhance REM sleep in humans and other mammals (DeGennaro et al., Int. J. Neurosci.82:163–8, 1995; Merchant-Nancy et al., Brain Res. 681:15–22, 1995; Vazquez et al., Sleep 21:138–42, 1998). Such changes in REM sleep do not appear to be modality-dependent, as auditory, somatosensory, and visual stimuli enhance REM to similar degrees (ibid). This Example shows that sensory stimuli, in the form of light presented to a non-ocular site during sleep, results in acute changes in REM sleep during the stimulus interval.

Methods

A total of 16 individuals were studied on two occasions, separated by at least 10 days. During one lab session, subjects were exposed to a 3-hr light stimulus during sleep; the other session was identical with the exception that a sham light stimulus was administered during sleep instead. The clock times of active and control light exposure were matched for each individual. Following an adaptation night in the laboratory, 4 of the 16 individuals studied were exposed to the stimulus during one sleep period at each session; the other 12 subjects were exposed to the stimulus on two consecutive nights at each session. Polysmnography (PSG) was recorded throughout each of the sleep episodes in which a light stimulus was administered.

The protocols were approved by the Institutional Review Board of Weill Medical College of Cornell University, and participants gave written informed consent prior to participation in each laboratory session.

In the active condition, one fiber optic light source (Biliblanket Plus Phototherapy System, Ohmeda Inc.) which emitted approximately 13,000 lux was placed on the popliteal fossa of each leg prior to bedtime. Each light delivery device consists of a halogen lamp in a vented metal housing, which also contains a small fan to disperse heat generated by the lamp. Illumination from the halogen bulb leaves the housing through 2400 optic fibers encased in a flexible plastic tube. The optic fibers terminate in a woven pad, approximately 10 cm×15 cm and 0.64 cm thick, that provides illumination without generating heat. The light pads were completely covered by athletic bandages wrapped around the legs. Automatic timers activated the light delivery devices at predetermined clock times and extinguished them 3 hours later. In the control condition, the light pads were placed in a manner identical to the active condition, with the exception that opaque black fabric sheaths were placed over the pads to insure that no light reached the skin. While the clock times of light exposure were identical for the active and control sessions for a given subject, the 3-hr. light interval was scheduled to occur at a variety of clock times across subjects. Thus, sleep and light exposure occurred at varying times throughout the 24-hour day.

A total of 28 pairs of PSG records (i.e., matched pairs of active and control light nights from the 16 subjects), were scored according to standard criteria (Rechtschaffer and Kales, A manual of standardized terminology, techniques and scoring system for sleep stages of human subjects, Washington, DC: National Institute of Health, 1968 vol., publ. 204) in 30-sec epochs by trained scorers who were blind to subject and condition. Because the primary aim of this study was to assess the effects of extraocular light presented during sleep, if the proportion of time spent asleep during the light interval was less than 80%, or if the proportion of time spent asleep throughout the entire sleep period (from sleep onset to terminal awakening) was less than 80%, the data from that night and the subject's matching record from the corresponding condition were excluded from analysis. Application of this criterion resulted in the exclusion of 5 pairs of records from analysis. The remaining 23 matched pairs of records included in all analyses were from 14 subjects (mean age 37.4 years, range 25–68 years; 13M, 1F).

Primary analyses focused on whether sleep was altered during the light stimulus administration. Of secondary interest was whether there were changes in sleep following the light stimulus interval. Thus, sleep parameters were compared across active and control conditions first for the 3-hr light versus sham stimulus interval and then across the post-stimulus intervals. The frequency and duration of discrete episodes of REM sleep (Webb and Dreblow, Sleep, 5:372, 1982) were similarly analyzed for the segments of sleep that occurred during the light stimulus interval and post-lights. Of interest with regard to the REM/NREM cycle length was the change in cycle length within the sleep period during which active lights were administered, from pre-, to during-, to post-light stimulation. Therefore, the REM/NREM cycle length across the sleep period relative to light administration was analyzed. In addition, a comparison of the length of REM/NREM cycles that occurred completely within the light stimulus intervals between active and control conditions was performed.

Results

Figure 5:
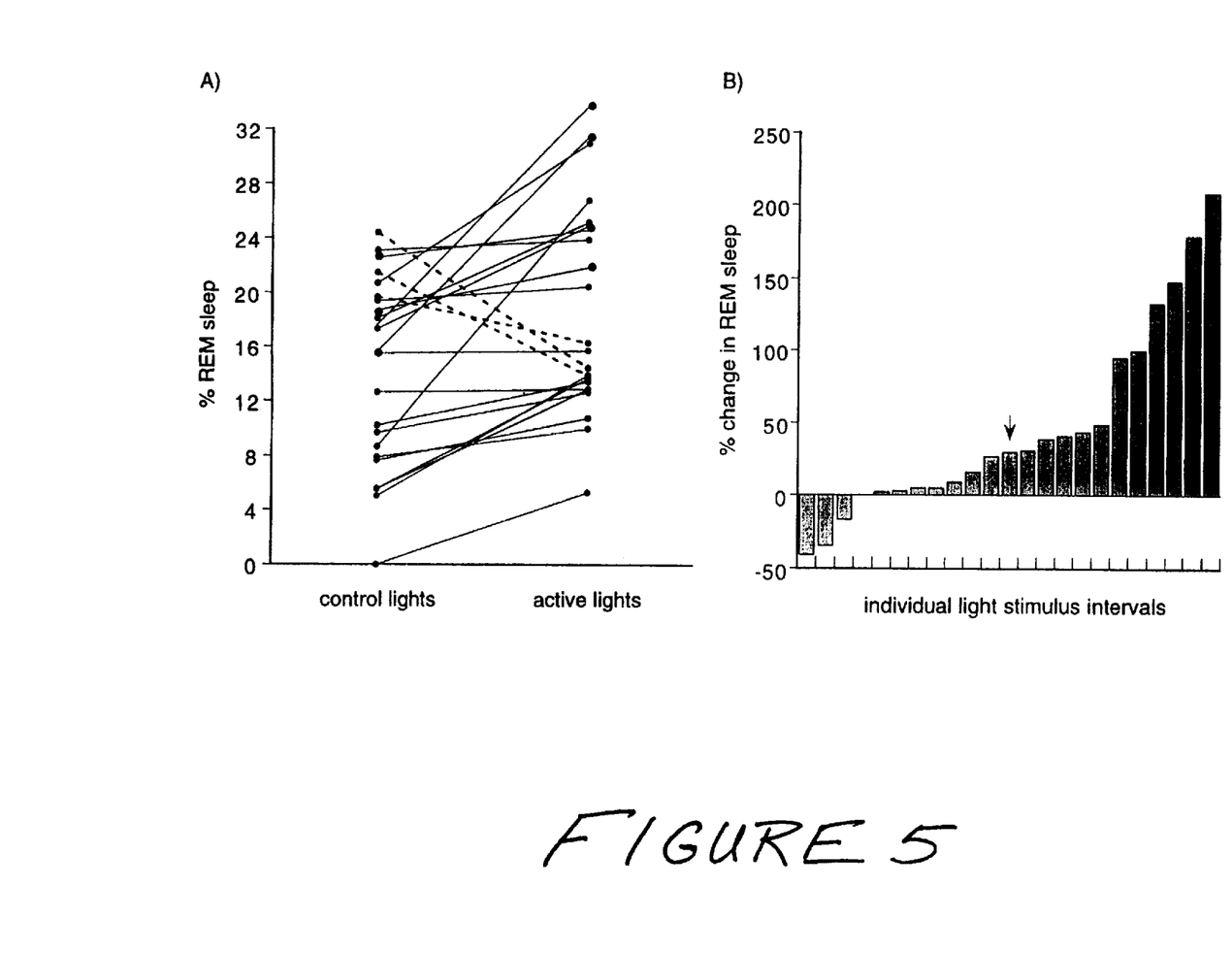
FIG. 5A and 5B. (A) Difference in the percentage of REM sleep during light exposure in control versus active conditions. Values from matched control and active sessions are connected. Dotted lines indicate the three light stimulus intervals during which the percentage of REM sleep was decreased in active relative to control sessions. The wide range of percent REM values (e.g., 0–44% for control intervals) reflects the fact that, while the clock times of light exposure were identical for the active and control sessions for a given subject, the 3-hr light stimulus intervals occurred at varying clock times/circadian phases across subjects, i.e., at times during which the propensity for REM sleep is both high and low. (B) Percentage change in minutes of REM sleep during the light stimulus interval for individual subjects, arranged in order of magnitude, from −41% to +209%. The median change in minutes of REM during light exposure was an increase of 30%; denoted by arrow. The mean change was +47%.

Comparisons of sleep stage variables across experimental conditions indicated that the number of minutes spent in REM during the 3-hour light interval increased significantly from a group average of 27.0±13 min in the control condition to 35.5±14 min in the active condition (t(22)=3.06, p<0.01). This 8.5 minute change in the group average represents a 31% increase in REM sleep over control levels. The significant increase in percentage of REM was observed in 12 of the 14 subjects studied (in 19 of the 23 matched pairs of sleep periods) (binomial test p(12)=0.006). Nearly two-thirds of the subjects (9 out of 14) exhibited increases in REM greater than the group average. For individual subjects, the absolute change in minutes of REM ranged from −19 to +35 during light exposure (see FIG. 5A). The percentage change in REM sleep from the control to the active condition averaged 47% and ranged from −41% to +209% (median=+43%) (FIG. 5B).

Only REM sleep was significantly altered by light administration. The increase in REM was accompanied by small decreases in wakefulness and all NREM sleep stages (Table 1). None of the changes in other sleep stages or in wakefulness during the light interval was significant. In addition, the changes in sleep were limited to the light stimulus interval. There were no differences in the amount of wakefulness or in any stage of sleep prior to or following light administration (Table 1).

TABLE 1

Sleep stage variables for segments of sleep periods occurring before, during, and after a 3-hr interval of light exposure to the popliteal fossa of human subjects during sleep.

| Sleep period segment (relative to light exposure interval) | Percent (SD) of polysomnographically-scored sleep stage* | | | | |
|---|---|---|---|---|---|
| | Wake | 1 | 2 | 3/4 | 5 |
| pre-lights | | | | | |
| Control | 35 (34) | 6 (4) | 26 (14) | 26 (18) | 8 (9) |
| Active | 31 (28) | 7 (7) | 28 (14) | 26 (21) | 8 (12) |
| during lights | | | | | |
| Control | 12 (10) | 6 (3) | 41 (11) | 27 (15) | 14 (5) |
| Active | 8 (5) | 6 (3) | 38 (14) | 28 (17) | 20 (6) |
| post-lights | | | | | |
| Control | 15 (12) | 9 (9) | 44 (12) | 11 (7) | 21 (11) |
| Active | 17 (24) | 6 (4) | 42 (20) | 11 (9) | 24 (20) |
| entire sleep period | | | | | |
| Control | 11 (5) | 6 (2) | 41 (11) | 24 (12) | 21 (6) |
| Active | 14 (8) | 6 (2) | 41 (8) | 25 (13) | 18 (5) |

*Wake and sleep stage percentages expressed as a proportion of minutes during the indicated segment (e.g., for entire sleep period, percentages were calculated as: (minutes of stage X/minutes from bedtime until final awakening) × 100).

Likewise, for those subjects who received light pulses on two consecutive nights, there were no first versus second night differences in sleep. While, as expected, the absolute amount of REM was influenced by the time of day during which the light stimulus occurred, the enhancement of REM sleep was not time-of-day dependent (i.e., REM sleep enhancement occurred during times when the propensity for REM sleep is both high and low).

Figure 6:
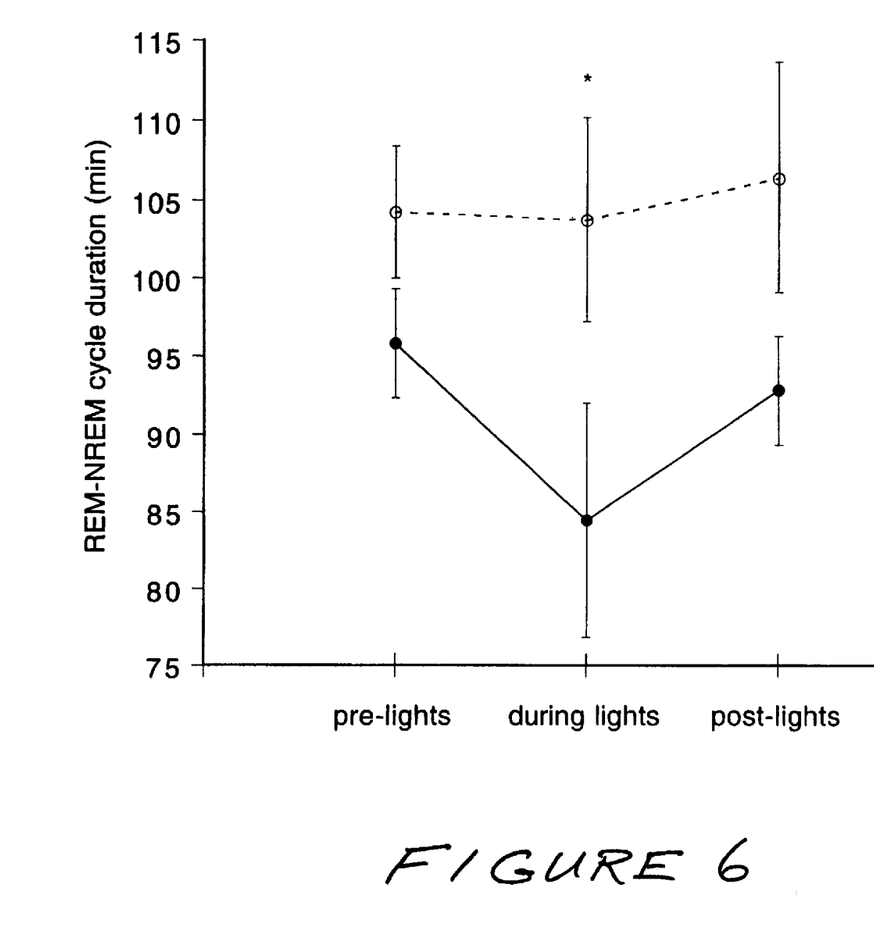
FIG. 6. REM/NREM cycle length in active versusl control conditions for the segments of sleep that occurred prior to, during, and after administration of 3 hours of extraocular light during sleep. Only cycles that occurred completely within the period indicated were analyzed (e.g., cycles included in the "pre-lights" cycle length average started and ended in the period before light exposure commenced). Mean cycle length was significantly shorter during light administration relative to the pre- and post-light cycles within the active condition as well as compared to the light stimulus interval in the control condition (*<0.05).

The mean duration of individual REM periods (REMP) during the control versus the active condition did not differ (22.4±12.4 min vs. 22.8±13.5 min, n.s.). Rather, the observed augmentation of REM sleep was due to an increase in the number of discrete REM sleep episodes that occurred during the 3-hour light stimulus intervals (Wilcoxon signed rank test of REM episode frequency in the control vs. active light conditions: 1.17±0.72 vs. 1.59±0.59 episodes; z=2.11, p<0.05). The number of REM periods occurring in the rest of the sleep period (i.e., before lights on and following lights off) did not differ between conditions. The increase in REM period frequence necessarily resulted in a shortening of the REM/NREM cycle length during the fixed duration light stimulus interval (FIG. 6). Indeed, an unpaired t-test comparing the duration of REM/NREM cycles that occurred completely within the light stimulus interval revealed that the mean cycle length was significantly shorter during the active (n=14; 84.4±7/6 min) than during the control condition (n=11; 103.7±6.5 min) (t(23)=2.33, p<0.05). The mean REM/NREM cycle length did not differ as a function of condition either prior to or following the light stimulus interval (FIG. 6).

While, as expected, the absolute amount of REM sleep obtained in a given sleep period was influenced by the time of day/circadian phase during which the sleep period and the light stimulus occurred, the enhancement of REM sleep was not time-of-day dependent. That is, REM sleep enhancement occurred during times when the propensity for REM sleep is both high and low. For example, three individuals who received a light pulse at either 2200-0100h, 0500-0800h, or 1630-1930h, exhibited changes in percentage of REM sleep during the light interval of +30%, +39%, and +44%, respectively.

Comparisons of sleep variables on the first versus second night of light administration (for the 9 subjects who received light pulses on two consecutive nights) revealed no significant night-to-night differences. The lack of night-to-night variation in sleep parameters in the active condition suggests that there was no "habituation effect" to the photic stimulus, as there was no decrease in REM sleep amounts from the first to the second stimulus periods.

Because extraocular light administration affects the circadian timing system in vertebrates, including humans (Campbell and Murphy, Science, 279:376, 1998; Underwood and Groos, Experientia, 38:989, 1982), it is conceivable that the increase of REM sleep was due to an immediate shift in the timing of REM sleep, either within or following the light exposure interval. To evaluate the possible immediate effects of extraocular light exposure on REM period timing, the latency from lights-on to the first occurrence of REM sleep during the first light presentation was calculated. The timing of the first REM period during light administration did not differ between active and control conditions (control: 63±50 min vs. active: 62±36 min, n.s.), suggesting that a shift in the timing of REM sleep was not responsible for the observed enhancement of REM sleep during light exposure. Moreover, an immediate phase shift (advance or delay) in REM sleep expression would presumably result in differences in the amount of REM sleep or distribution of REM periods not only during the 3-hr light interval, but in the remainder of the sleep period following light exposure, as well. Such was not the case (Table 1; FIG. 6).

Preliminary analysis of four subjects' data, who were exposed to light throughout their sleep periods (as opposed to the 3-hour exposures described in the paper), revealed that REM sleep continued to be enhanced by an average of about 30%.

Discussion

The data reported here provide additional, strong evidence that light presented to a site other than the eye is transduced into a signal that can influence brain function. Unexpectedly, in this case, the light signal administered to a peripheral site was transmitted to brain structures involved in REM sleep. Thus, surprisingly like other modes of sensory stimulation (DeGennaro et al., supra; Merchant-Nancy et al., supra; Vazquez et al., supra), extra-ocular light presented to sleeping subjects had a significant effect on REM sleep. The known modes to alter REM sleep generally increase the REM period. In contrast, at least in some cases, the present invention increases REM frequency, although the ability of extraocular light to increase the REM period must be considered.

There is ample evidence to indicate that photoreceptors exist in the largest sense organ—the skin—and that the sequelae of phototransduction via dermal light receptors includes effects on central nervous system processes and on behavior (Steven, Biol. Rev. (Camb. Philos. Soc.) 38:204, 1963; Tosini and Avery, Physiol. Beh. 59:195, 1996; Ullen et al., Behav. Brain Res. 54:107, 1993). In the current study, the light signal administered to a peripheral site during sleep was transmitted to the central nervous system and influenced the generation of REM sleep. The enhancement of REM sleep observed during exposure to extraocular light in this study appears to reflect an acute effect of light administration on the REM sleep generating system, rather than a "downstream" result of manipulating the circadian clock.

These results may be explained by several possible mechanisms. Cholinergic pathways that are activated by sensory stimuli (Merchant-Nancy, et al., Brain Res. 681:15–22, 1995), and possibly involved in the transduction of photic information to the circadian timing system (Earnest, el al., Proc. Nat'l. Acad. Sci. USA, 82:4277–81, 1985) could account in part for both the observed effects on REM sleep as well as the phase-shifting effects of extra-ocular light in awake individuals (Campbell, et al., Science, 279:376–9, 1998). Alternatively, serotonergic modulation of responses to light (Challet, et al., J. Biological Rhythms, 13:410–21, 1998), as well as serotonergic transmission from the dorsal raphe during sleep (Meyer-Bernstein, et al, J. Neurosci., 16:2097–1111, 1996) might underlie the REM enhancement resulting from administration of light to sleeping humans.

With regard to the effects of decreased REM sleep, it is well-established that experimentally induced REM sleep deprivation in animals and humans has detrimental effects on memory (Smith, Neurosci. Biobeh. Rev. 9:157, 1985; Vogel, Arch. Gen. Psychiatry, 32:749, 1975). Further, while there are only slight decreases in typical REM sleep amounts in healthy older humans relative to their younger counterparts, a significant decrease in the proportion of REM sleep, as well as a delay in the onset of the first REM period, are hallmarks of age-related dementing disorders (Montplaisir et al., Sleep, 18:145, 1995). Indeed, the proportion of REM sleep, REM density (i.e., the number of rapid eye movements per unit of time), and REM latency have been used to distinguish normal, depressed, and demented older individuals (Dykierek et al., J. Psychiatric Res. 32:1, 1998; Vitiello et al., Biol. Psychiatry, 19:721, 1984).

That REM sleep is altered in demented patients is consistent with the "cholinergic hypothesis" of Alzheimer's disease, which posits that a deficiency in cholinergic transmission and/or production in the central nervous system is responsible for many of the symptoms of the disease. Accordingly, the treatment of dementia in Alzheimer's disease relies heavily on cholinomimetic agents and aceylcholinesterase inhibitors (Peskind, J. Clin. Psychiatry 59 (Suppl. 9):22, 1998; Polinsky, Clinical Therapeutics 20:634, 1998). These drugs have also been shown to enhance REM sleep (Holsboer-Trachsler et al., Neurophyschopharm. 8:87, 1993; Riemann et al., Psychiatry Res. 51:253, 1994), a feature that places them among the few means by which REM sleep can be augmented. Yet, the decreased metabolism of drugs in aging, as well as an increased risk of side effects and multiple drug interactions in the elderly make nonpharmacological therapies attractive for this population. Thus while cholinergic drugs may effectively increase REM sleep and also attenuate symptoms of dementia, a non-invasive, non-pharmacological technique by which this could be accomplished is highly desirable. In this regard, the finding that REM sleep is enhanced during extraocular light exposure can be utilized to develop a novel approach to ameliorating symptoms of dementia.

In the current study, administration of extraocular light resulted in an average increase in REM sleep of 31% during the light exposure interval. This degree of enhancement is comparable to or larger than the increase in REM sleep following administration of cholinergic agents, DHEA, or other modalities of sensory stimulation. Means of augmenting REM sleep are rare, warranting elaboration of the initial discovery.

A longer interval of light exposure led to proportional increases in REM sleep. Previous studies in which REM sleep was altered by sensory stimulation have yielded results suggesting that determinants of the manner in which REM sleep is influenced are numerous and complex. For example, sensory stimuli have been reported to alter REM period frequency, REM period duration, or phasic REM events (e.g. eye movements, muscle twitches). The effect on REM sleep induced by sensory stimulation appears to depend on several factors, including pre-sleep brain activation levels, stimulation modality, the timing of sensory stimulation relative to individual rapid eye movements, and whether or not the sleep period was preceded by an intensive learning session. A study using auditory stimulation for varying durations and across multiple sleep periods in rats indicated that there was no habituation effect, which is consistent with our observation that further increases in REM sleep are possible with more prolonged non-ocular light stimulation.

Further analyses of these data focused on the composition of sleep, particularly the effects of extra-ocular light on the frequency, duration, and consolidation of discrete REM periods, may elucidate additional benefits of this treatment. In addition, relationships between circadian phase-resetting effects and alterations in sleep resulting from administration of extra-ocular light during sleep may be examined.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

All patents, patent applications, publications, and other materials cited herein are hereby incorporated by reference in their entireties.

What is claimed is:

1. A method for enhancing REM sleep in a subject, which method comprises exposing a non-ocular region of a subject to non-solar photic stimulation for an interval during a sleep period such that REM sleep is enhanced, wherein the REM sleep is enhanced with minimum impact on the circadian clock.

2. The method according to claim 1, wherein enhancing REM sleep comprises increasing the number of minutes spent in REM sleep during the interval of photic stimulation.

3. The method according to claim 2, wherein the number of minutes in REM sleep increases by at least about 30%.

4. The method according to claim 2, wherein the number of minutes in REM sleep increases by at most about 200%.

5. The method according to claim 1, wherein enhancing REM sleep comprises increasing the frequency of REM periods during the interval of photic stimulation.

6. The method according to claim 5, wherein the frequency of REM periods increases by about 40%.

7. The method according to claim 1, wherein the non-ocular region is a region of ample surface vasculature.

8. The method according to claim 7, wherein the region of ample surface vasculature is the popliteal fossa.

9. The method according to claim 1, wherein the interval lasts for a duration ranging from between about 15 minutes to about 12 hours.

10. The method according to claim 9, wherein the duration is about three hours.

11. The method according to claim 1, wherein the photic stimulation has an intensity ranging from about 15 lux to about 150,000 lux.

12. The method according to claim 11, wherein the photic stimulation has an intensity ranging from about 10,000 lux to about 13,000 lux.

13. The method according to claim 1, wherein the photic stimulation has a bandwidth in the visible spectrum.

14. The method according to claim 13, wherein the photic stimulation has a bandwidth between about 455 nanometers (nm) and 540 nm.

15. The method of claim 1, which method further comprises enhancing cognitive function in a subject.

16. The method according to claim 15, wherein the subject suffers from a medical disorder in which mental status is compromised.

17. The method according to claim 15, wherein the subject is a normal individual.

18. The method according to claim 15, wherein cognitive function is enhanced to a degree comparable to that achieved with a cholinergic agonist.

19. The method of claim 1, wherein exposure to photic stimulation occurs both before and after the daily minimum body temperature.

20. A method for extending a REM cycle of a person, comprising the steps of:
 a) sensing the start of the REM cycle;
 b) sensing the end of the REM cycle;
 c) determining the time interval of the REM cycle; and
 d) augmenting the time interval of the REM cycle by selectively providing non-ocular photic stimulation for a predetermined interval.

21. An article for extending a REM cycle of a person, comprising:
 a) a sensor which provides phasic activity signals;
 b) a timing circuit connected to the sensor and outputting an elapsed-interval signal indicative of the magnitude of the REM cycle;
 c) a comparator which compares the elapsed-interval signal to a predetermined-interval signal and outputs a shortfall signal;
 d) a controller responsive to the shortfall signal to generate a control signal;
 e) a photic stimulator positionable in contact with the person's skin and being actuated in response to the control signal.

22. The article as in claim 21, wherein the controller further generates an update signal which is provided to the comparator as the predetermined-interval signal during a subsequent REM cycle.

* * * * *